United States Patent
Kitagawa et al.

(10) Patent No.: US 9,670,127 B2
(45) Date of Patent: Jun. 6, 2017

(54) POROUS COORDINATION POLYMER AND APPLICATION THEREFOR

(71) Applicant: Kyoto University, Kyoto (JP)

(72) Inventors: Susumu Kitagawa, Kyoto (JP); Masakazu Higuchi, Kyoto (JP); Prabhakara Rao Koya, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 15/120,898

(22) PCT Filed: Feb. 24, 2015

(86) PCT No.: PCT/JP2015/055228
§ 371 (c)(1),
(2) Date: Aug. 23, 2016

(87) PCT Pub. No.: WO2015/129685
PCT Pub. Date: Sep. 3, 2015

(65) Prior Publication Data
US 2016/0362359 A1    Dec. 15, 2016

(30) Foreign Application Priority Data
Feb. 26, 2014   (JP) .................................. 2014-035914

(51) Int. Cl.
*C07C 63/331*   (2006.01)
*B01J 20/22*    (2006.01)
(Continued)

(52) U.S. Cl.
CPC .......... *C07C 63/331* (2013.01); *B01J 20/226* (2013.01); *C07F 3/06* (2013.01); *C09D 5/00* (2013.01); *C09D 7/1233* (2013.01); *C09K 3/32* (2013.01)

(58) Field of Classification Search
CPC . C09D 5/00; C09D 7/1233; C09K 3/32; B01J 20/226; C07C 63/331; C07F 3/06
(Continued)

(56) References Cited

FOREIGN PATENT DOCUMENTS

| CN | 101481457 | 7/2009 |
|----|-----------|--------|
| JP | 2006-503946 | 2/2006 |

(Continued)

OTHER PUBLICATIONS

Aguado, et al., "Engineering structured MOF at nano and macroscales for catalysis and separation", J. Mater. Chem., 2011, 21, 7582-7588.

(Continued)

*Primary Examiner* — Porfirio Nazario Gonzalez
(74) *Attorney, Agent, or Firm* — Cesari and McKenna, LLP

(57) ABSTRACT

An object of the present invention is to provide a novel porous coordination polymer having superhydrophobicity. The present invention relates to a porous coordination polymer comprising:
  a divalent or trivalent metal ion; and
  an organic ligand represented by the following formula (1):

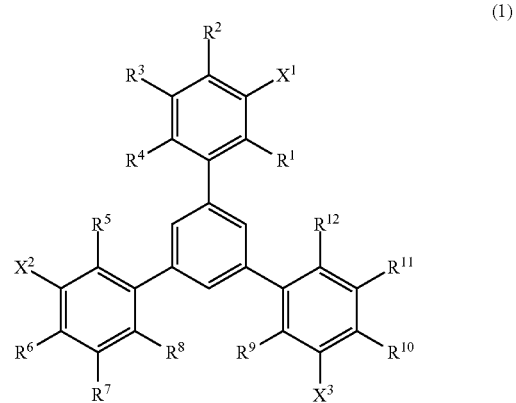

wherein $X^1$, $X^2$, and $X^3$ are the same or different, and each represent $CO_2^-$, $CS_2^-$, $PO_3^{2-}$, $PO_4^{2-}$, $AsO_3^{2-}$, $AsO_4^{2-}$, $SO_3^-$, $SO_4^-$, $SeO_3^-$, $SeO_4^-$, $TeO_3^-$, or $TeO_4^-$; and
$R^1$, $R^2$, $R^3$, $R^4$, $R^5$, $R^6$, $R^7$, $R^8$, $R^9$, $R^{10}$, $R^{11}$, and $R^{12}$ are the same or different, and each represent hydrogen or $C_{1-20}$ alkyl;

(Continued)

the metal ion and the organic ligand being alternately linked by a coordinate bond.

12 Claims, 8 Drawing Sheets

(51) Int. Cl.
    *C07F 3/06*     (2006.01)
    *C09D 5/00*     (2006.01)
    *C09D 7/12*     (2006.01)
    *C09K 3/32*     (2006.01)

(58) Field of Classification Search
    USPC .......................................... 556/119, 130, 132
    See application file for complete search history.

(56) References Cited

FOREIGN PATENT DOCUMENTS

| JP | 2007-516221 | 6/2007 |
| WO | WO-2004/037895 | 5/2004 |
| WO | WO-2004/101575 | 11/2004 |

OTHER PUBLICATIONS

Chen, et al., "Superhydrophobic perfluorinated metal-organic frameworks", Chem. Commun., 2013, 49, 6846-6848.
He, et al., "Novel $C_3$-symmetrical triphenylbenzene-based organogelators with different linkers between phenyl ring and alkyl chain", Tetrahedron, 66 (2010) 3553-3563.
Nguyen, et al., "Moisture-Resistant and Superhydrophobic Metal-Organic Frameworks Obtained via Postsynthetic Modification", J. Am. Chem. Soc., Apr. 7, 2010; 132(13): 4560-4561.

POROUS COORDINATION POLYMER AND APPLICATION THEREFOR

CROSS REFERENCE TO RELATED APPLICATIONS

This application is the National Stage of International Application No. PCT/JP2015/055228, filed on Feb. 24, 2015, which claims priority to Japanese Application No. 2014-035914, filed on Feb. 26, 2014. The content of both applications are hereby incorporated by reference in their entirety.

TECHNICAL FIELD

The present invention relates to a porous coordination polymer and applications thereof.

BACKGROUND ART

"Superhydrophobic surfaces" are not scientifically defined; however, superhydrophobic surfaces generally refer to surfaces that have a water contact angle of 150° or more and are hardly wetted with water. It is generally known that a solid surface formed from a low-surface-energy substance comprising fluorine, etc., as a main component can have excellent hydrophobicity. It is also known that the hydrophobicity is further increased by imparting appropriate roughness to the surface.

Meanwhile, compounds having pores in a solid structure are called porous compounds. Various porous materials, such as organic substances and inorganic substances, are known. Typical examples thereof include zeolite, activated carbon, silica gel, molecular sieves, and the like. Porous coordination polymers (PCPs) have recently attracted attention as new porous materials. Porous coordination polymers are materials that form porous structures by taking advantage of the coordinate bonds between metal ions and organic ligands. They are expected to find application in gas storage or separation, catalysts, etc. However, many porous coordination polymers reported to date have limited practical applicability due to their low stability in water and propensity for degradation upon exposure to water.

Accordingly, in order to improve the stability of porous coordination polymers in water, attempts have been made to impart (super) hydrophobicity to the surface of porous coordination polymers. NPL 1 teaches that PCP comprising a fluorinated aromatic ring as an organic ligand achieves a contact angle of 151±1°. NPL 2 and NPL 3 teach that PCP comprising a compound terminated with bulky alkyl chains as an organic ligand achieves a contact angle of more than 150°.

CITATION LIST

Non-Patent Literature

NPL 1: T.-H. Chen, I. Popov, O. Zenasni, O. Daugulis, O. Š. Miljanić, Chem. Commun., 2013, 49, pp. 6846-6848

NPL 2: J. G. Nguyen, S. M. Cohen, J AM Chem Soc, 2010, 132, pp. 4560-4561

NPL 3: S. Aguado, J. Canivet, D. Farrusseng, J Mater Chem, 2011, 21, pp. 7582-7588

SUMMARY OF INVENTION

Technical Problem

Under the above-stated circumstances, the problem to be solved by the present invention is to provide a novel porous coordination polymer having superhydrophobicity.

Solution to Problem

The present inventors conducted extensive research to develop a novel porous coordination polymer having superhydrophobicity, and consequently found that a porous coordination polymer having superhydrophobicity can be produced by using an aromatic ring having a specific structure as an organic ligand, and that the above problem can be solved. The present invention has been completed based on this finding.

Specifically, the present invention relates to porous coordination polymers, a hydrophobic coating agent, and an adsorbent shown in the following items 1 to 6.

Item 1. A porous coordination polymer comprising:
a divalent or trivalent metal ion; and
an organic ligand represented by the following formula (1):

wherein $X^1$, $X^2$, and $X^3$ are the same or different, and each represent $CO_2^-$, $CS_2^-$, $PO_3^{2-}$, $PO_4^{2-}$, $AsO_3^{2-}$, $AsO_4^{2-}$, $SO_3^-$, $SO_4^-$, $SeO_3^-$, $SeO_4^-$, $TeO_3^-$, or $TeO_4^-$; and $R^1$, $R^2$, $R^3$, $R^4$, $R^5$, $R^6$, $R^7$, $R^8$, $R^9$, $R^{10}$, $R^{11}$, and $R^{12}$ are the same or different, and each represent hydrogen or $C_{1-20}$ alkyl;

the metal ion and the organic ligand being alternately linked by a coordinate bond.

Item 2. The porous coordination polymer according to item 1, wherein the organic ligand is a compound represented by the formula (1) wherein $X^1$, $X^2$, and $X^3$ are all $CO_2^-$; and $R^1$, $R^2$, $R^3$, $R^4$, $R^5$, $R^6$, $R^7$, $R^8$, $R^9$, $R^{10}$, $R^{11}$, and $R^{12}$ are all hydrogen.

Item 3. The porous coordination polymer according to item 1, wherein the metal ion is a transition metal ion.

Item 4. The porous coordination polymer according to item 1, wherein the metal ion is at least one member selected from the group consisting of zinc ions, nickel ions, and cobalt ions.

Item 5. A hydrophobic coating agent comprising the porous coordination polymer according to any one of items 1 to 4.

Item 6. An adsorbent for an organic solvent or oil, comprising the porous coordination polymer according to any one of items 1 to 4.

Advantageous Effects of Invention

The porous coordination polymer of the present invention has a water contact angle of 150° or more, and has super-hydrophobicity; therefore, it is useful as a hydrophobic coating agent. Moreover, the porous coordination polymer of the present invention can selectively adsorb aromatic organic solvents, such as benzene and toluene; therefore, it can selectively remove an organic solvent from water.

DESCRIPTION OF EMBODIMENTS

The porous coordination polymer of the present invention comprises:
a divalent or trivalent metal ion; and
an organic ligand represented by the following formula (1):

wherein $X^1$, $X^2$, and $X^3$ are the same or different, and each represent $CO_2^-$, $CS_2^-$, $PO_3^{2-}$, $PO_4^{2-}$, $AsO_3^{2-}$, $AsO_4^{2-}$, $SO_3^-$, $SO_4^-$, $SeO_3^-$, $SeO_4^-$, $TeO_3^-$, or $TeO_4^-$; and
$R^1$, $R^2$, $R^3$, $R^4$, $R^5$, $R^6$, $R^7$, $R^8$, $R^9$, $R^{10}$, $R^{11}$, and $R^{12}$ are the same or different, and each represent hydrogen or $C_{1-20}$ alkyl;
the metal ion and the organic ligand being alternately linked by a coordinate bond.

Examples of the divalent or trivalent metal ion constituting the porous coordination polymer include magnesium ions, calcium ions, barium ions, scandium ions, lanthanoid ions, titanium ions, zirconium ions, vanadium ions, chromium ions, manganese ions, iron ions, cobalt ions, nickel ions, copper ions, zinc ions, cadmium ions, aluminum ions, and the like. Among these metal ions, transition metal ions, such as scandium ions, lanthanoid ions, titanium ions, zirconium ions, vanadium ions, chromium ions, manganese ions, iron ions, cobalt ions, nickel ions, copper ions, zinc ions, and cadmium ions, are preferred; and cobalt ions, nickel ions, and zinc ions are more preferred. Although a single metal ion is preferable, two or more metal ions may be contained. Moreover, porous coordination polymers used in the present invention can be used singly or in a mixture of two or more.

The porous coordination polymer contains an organic ligand represented by the above formula (1). In the formula (1), $X^1$, $X^2$, and $X^3$ are portions to which the metal ions are coordinated with an unshared electron pair, and can be selected from $CO_2^-$, $CS_2^-$, $PO_3^{2-}$, $PO_4^{2-}$, $AsO_3^{2-}$, $AsO_4^{2-}$, $SO_3^-$, $SO_4^-$, $SeO_3^-$, $SeO_4^-$, $TeO_3^-$, and $TeO_4^-$. $X^1$, $X^2$, and $X^3$ may be the same or different. $X^1$, $X^2$, and $X^3$ are preferably $CO_2^-$.

$R^1$, $R^2$, $R^3$, $R^4$, $R^5$, $R^6$, $R^7$, $R^8$, $R^9$, $R^{10}$, $R^{11}$, and $R^{12}$ are each hydrogen or $C_{1-20}$ alkyl. $R^1$, $R^2$, $R^3$, $R^4$, $R^5$, $R^6$, $R^7$, $R^8$, $R^9$, $R^{10}$, $R^{11}$, and $R^{12}$ may be the same or different.

Examples of $C_{1-20}$ alkyl include $C_{1-20}$ linear or branched alkyl, such as methyl, ethyl, n-propyl, isopropyl, n-butyl, isobutyl, tert-butyl, n-hexyl, n-octyl, n-decyl, lauryl, myristyl, cetyl, stearyl, and icosyl; and $C_{1-4}$ linear alkyl is preferred.

The organic ligand is preferably a compound represented by the above formula (1) wherein $X^1$, $X^2$, and $X^3$ are all $CO_2^-$, and $R^1$, $R^2$, $R^3$, $R^4$, $R^5$, $R^6$, $R^7$, $R^8$, $R^9$, $R^{10}$, $R^{11}$, and $R^{12}$ are all hydrogen. Specific examples thereof include anions ($BTMB^{3-}$) derived from 1,3,5-tris(3-carboxyphenyl) benzene ($H_3BTMB$).

The greatest feature of the porous coordination polymer of the present invention is the use of a compound having a structure represented by the formula (1) as an organic ligand. In the organic ligand used in the present invention, benzene rings linked to 1-, 3-, and 5-positions of benzene each have, in the meta position, a group to which the metal ion is coordinated. Due to the use of an organic ligand having such a structure, a fine rugged structure (periodic roughness) can be formed on a solid surface. As a result, a water contact angle of more than 150° can be achieved. According to the present invention, superhydrophobicity has been achieved for the first time by using an organic ligand comprising an aromatic hydrocarbon, as represented by the formula (1), without using conventionally known low-surface-energy substances (e.g., fluorinated aromatic compounds and compounds terminated with bulky alkyl chains).

The porous coordination polymer used in the present invention can be produced by reacting an organic ligand represented by the formula (1) with at least one metal salt selected from divalent or trivalent metal salts in the vapor, liquid, or solid phase. In particular, it is preferable to produce the porous coordination polymer by reacting them in a solvent under ordinary pressure for several hours to several days for precipitation. In this case, the reaction may be performed under irradiation of ultrasonic waves or microwaves.

Examples of salts of the divalent or trivalent metal used in the production of a porous coordination polymer include magnesium salts, calcium salts, barium salts, scandium salts, lanthanoid salts, titanium salts, zirconium salts, vanadium salts, chromium salts, manganese salts, iron salts, cobalt salts, nickel salts, copper salts, zinc salts, cadmium salts, aluminum salts, and the like. Among these metal salts, scandium salts, lanthanoid salts, titanium salts, zirconium salts, vanadium salts, chromium salts, manganese salts, iron salts, cobalt salts, nickel salts, copper salts, zinc salts, and cadmium salts are preferred; and cobalt salts, nickel salts, and zinc salts are more preferred. It is preferable to use a single metal salt; however, two or more metal salts may be used in combination. For such metal salts, organic acid salts, such as acetate and formate; and inorganic acid salts, such as sulfate, nitrate, carbonate, hydrochloride, and hydrobromate, can be used.

As for the mixing ratio of the metal salt and the organic ligand in the production of a porous coordination polymer, the molar ratio of metal salt to organic ligand is preferably 1:5 to 5:1, and more preferably 1:2 to 2:1.

When a porous coordination polymer is produced in a solvent, the molar concentration of the metal salt in the solvent is preferably 0.005 to 5 mol/L, and more preferably 0.01 to 2 mol/L. It is not preferable to perform the reaction at a concentration lower than this range because, although the target porous coordination polymer can be obtained, the yield decreases. At a concentration higher than this range, the unreacted metal salt remains, and it is difficult to purify the resulting porous coordination polymer.

When a porous coordination polymer is produced in a solvent, the molar concentration of the organic ligand in the solvent is preferably 0.001 to 5 mol/L, and more preferably 0.005 to 2 mol/L. It is not preferable to perform the reaction at a concentration lower than this range because, although the target porous coordination polymer can be obtained, the yield decreases. At a concentration higher than this range, the solubility decreases, and the reaction does not proceed smoothly.

As the solvent used in the production of a porous coordination polymer, an organic solvent, water, or a mixed solvent thereof can be used. Specific examples of organic solvents include alcohol compounds, such as methanol, ethanol, and propanol; ether compounds, such as diethyl ether, 1,2-dimethoxyethane, and tetrahydrofuran; aliphatic hydrocarbons, such as hexane, cyclohexane, and heptane; aromatic hydrocarbons, such as benzene and toluene; halogenated hydrocarbons, such as methylene chloride and chloroform; acetone, ethyl acetate, acetonitrile, N,N-dimethylformamide, and the like. Organic solvents or water can be used singly, and a mixed solvent thereof can also be used.

The reaction temperature in the production of a porous coordination polymer is preferably about room temperature to about 200° C.

The completion of the reaction to produce a porous coordination polymer can be confirmed by quantifying the amount of residual raw materials by gas chromatography or high-performance liquid chromatography; however, the method is not limited thereto. After completion of the reaction, the obtained mixed solution is subjected to suction filtration to collect the precipitate. After washing with an organic solvent, vacuum-drying is performed for several hours at a temperature at which the porous coordination polymer is not decomposed (e.g., 25 to 250° C.) Thus, the porous coordination polymer used in the present invention can be obtained. The operation of washing with an organic solvent and vacuum-drying can be replaced by washing with supercritical carbon dioxide, which is more effective.

The composition ratio of the components that constitute the porous coordination polymer can be confirmed by, for example, single crystal X-ray structure analysis, powder X-ray crystal structure analysis, or elemental analysis; however, the method is not limited thereto.

Before gas or the like is adsorbed into the pores of the porous coordination polymer, it is preferable to perform pre-drying under vacuum in order to remove the water or solvent adsorbed by the porous coordination polymer.

The porous coordination polymer of the present invention has a contact angle with water of 150° or more, and has superhydrophobicity; therefore, it is useful as a hydrophobic coating agent.

For example, the hydrophobic coating agent can be formed as a coating composition containing the porous coordination polymer of the present invention. The coating composition can be obtained by, for example, dispersing the porous coordination polymer of the present invention in a binder resin.

The porous coordination polymer and the binder resin in the coating composition may be mixed at a ratio that imparts sufficient hydrophobicity and ensures the strength or adhesion of the coated film. For example, about 5 to 900 parts by weight of the binder resin can be mixed with 100 parts by weight of the porous coordination polymer.

Examples of binder resins include various known resins, such as acrylic resin, acrylic silicone resin, acrylic urethane resin, polyester resin, epoxy resin, urethane resin, and fluororesin. These resins can be used singly or in a mixture of two or more.

Moreover, the coating composition may contain an organic solvent so as to increase the coating properties or adhesion when a hydrophobic coating layer is formed on a substrate to be coated. Examples of organic solvents include those containing one or more members selected from alcohol compounds, ketone compounds, ester compounds, alcohol ester compounds, ketone ester compounds, ether compounds, ketone alcohol compounds, ether alcohol compounds, ketone ether compounds, and ester ether compounds.

The coating composition may contain a leveling agent, a coupling agent, a thickener, an ultraviolet absorber, a light stabilizer, an antifreezing agent, etc., within a range that does not adversely affect the effects of the present invention. Various known additives can be used as these additives.

In the preparation of the hydrophobic coating agent of the present invention, in order to sufficiently disperse the porous coordination polymer in a binder resin, a device used to disperse or mix a coating composition, such as a bead mill or a high-speed rotary stirrer, is used.

The hydrophobic coating agent of the present invention can be coated on a substrate by, for example, coating or spraying. The coating method is not particularly limited. Examples thereof include conventionally known coating methods, such as a spin coating method, a dip coating method, a flow coating method, a spray coating method, a roll coating method, a screen printing method, a bar coater method, brush coating, and sponge coating. In order to improve adhesion, the substrate may be coated with an intermediate layer before coating with the hydrophobic coating agent.

The film thickness of a coated film formed by coating the hydrophobic coating agent of the present invention may be about 100 nm or more and about 2 μm or less, and preferably about 200 nm or more and about 1.5 μm or less. If the film thickness is overly thin, desired hydrophobicity cannot be realized. If the film thickness is overly thick, the strength of the coated film decreases.

Examples of the material of the substrate that can be coated with the hydrophobic coating agent of the present invention include metal, ceramics, glass, plastic, wood, stone, cement, concrete, fiber, fabric, paper, combinations thereof, laminates thereof, coated products thereof, and the like.

The hydrophobic coating agent of the present invention can be applied to various members, the surface of which requires drip-proof properties, anti-rust properties, draining properties, water-based stain adhesion-preventing properties, running-water cleaning properties, ice and snow accretion-preventing properties, and the like. Specific examples thereof include building exterior materials, such as outer walls and roofs; window frames; exterior and coating of vehicles, such as automobiles, rail cars, airplanes, vessels, bicycles, and motorcycles; soundproof walls, vinyl houses, insulators, covers for vehicles, tent materials, reflecting plates, sliding shutters, screen doors, covers for solar cells, covers for solar collectors such as solar water heaters, streetlights, pavements, exterior lighting, stones for artificial waterfalls or artificial fountains, tiles, bridges, greenhouses, exterior wall materials, sealers between walls or insulators, guardrails, verandas, vending machines, air-conditioner outdoor units, outdoor benches, various display devices, rolling shutters, tollgates, fare boxes, dustproof covers and coating, coating of mechanical devices or articles, exterior and coating of advertising towers, structural members, and films, emblems, and the like attachable to these articles.

Moreover, the hydrophobic coating agent of the present invention can also be applied to members for which transparent coated films are required, such as signboards, signs, direction signboards, bronze statues, sculptures, various designed materials, transparent plastic films, buildings, vehicles, window materials of various instruments, glasses, sunglasses, rear-view mirrors for vehicles, mirrors for bathrooms or washrooms, dental mirrors, road mirrors, optical lenses, endoscope lenses, goggles, and shields.

The porous coordination polymer of the present invention can selectively adsorb vapor; carbon dioxide; an aromatic organic solvent, such as benzene or toluene; and oil, such as olive oil, in its pores.

The outer surface of the porous coordination polymer of the present invention has superhydrophobicity, and the porous coordination polymer can selectively adsorb an aromatic organic solvent or oil in its pores; therefore, the porous coordination polymer of the present invention can be used as an adsorbent for separating an aromatic organic solvent or oil from water. The adsorbent is preferably composed only of the porous coordination polymer of the present invention, and it is possible for the adsorbent to contain other components within a range that does not adversely affect the adsorption effects.

EXAMPLES

The present invention is described in more detail below with reference to Examples and Comparative Examples. The present invention is not limited to the following Examples. The analysis and evaluation in the Examples were performed in the following manner.

In the Examples, the following reagents were directly used without purification.

$Zn(NO_3)_2 \cdot 4H_2O$ (produced by Merck Ltd.)
N,N-dimethylformamide (DMF) (produced by Nacalai Tesque, Inc.)
Methanol (MeOH) (produced by Nacalai Tesque, Inc.)
Benzene (produced by Nacalai Tesque, Inc.)
Toluene (produced by Nacalai Tesque, Inc.)
Cyclohexane (produced by Nacalai Tesque, Inc.)
Oil Blue 35 (produced by Nacalai Tesque, Inc.)

The analysis and evaluation in the Examples were performed in the following manner.

(1) Thermogravimetric Analysis (TGA)

Thermogravimetric analysis was conducted using a Rigaku TG8120 under flowing nitrogen at a heating rate of 10 $Kmin^{-1}$.

(2) Powder X-Ray Diffraction

Powder X-ray diffraction was conducted using a Rigaku RINT powder diffractometer with CuKα anode.

(3) Single Crystal X-ray Diffraction

Single crystal X-ray diffraction measurement was performed at 223 K using a Rigaku AFC10 diffractometer with Saturn Kappa CCD system equipped with a MicroMax-007 HF/VariMax rotating-anode X-ray generator with confocal monochromated MoKα radiation. Data were processed using Crystal Clear TM-SM (Version 1.4.0). The crystal structure was solved and refined using the WinGX suite of programs using SHELXS-97[1] or SHELXL-97[2].

(4) Gas Adsorption Isotherm

Gas adsorption isotherms were obtained using BELSORP-mini, BELSORP-max, and BELSORP-HP (high pressure) volume adsorbers (produced by MicrotracBEL Corp.). In the adsorption isotherms, filled-in symbols (e.g., ●) represent adsorption, and hollow symbols (e.g., ○) represent desorption.

(5) Water Adsorption Isotherm

Water adsorption isotherms were obtained using a BELSORP-max volume adsorber (produced by MicrotracBEL Corp.).

(6) Contact Angle

Contact angle measurements were recorded with a Panasonic model number: WV-CP480SDIII. Approximately 5 to 10 mg of powder was pressed onto a glass slide with a spatula. A drop of water was slowly dropped onto the sample with a microsyringe, and the contact angle was estimated using the CAM 100 software package.

Production Example 1 (Synthesis of 1,3,5-tris(3-carboxyphenyl)benzene ($H_3BTMB$))

Figure 1:
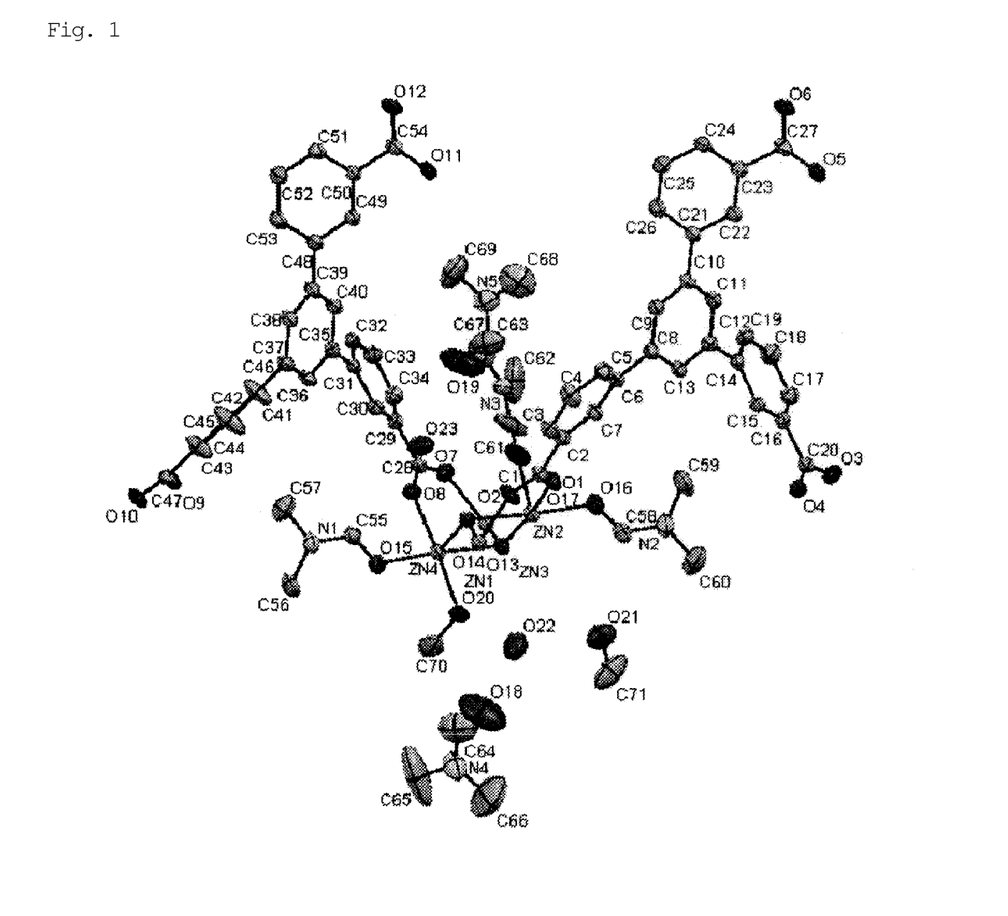
FIG. 1 shows an ORTEP diagram of a porous coordination polymer (1) obtained in Example 1.

$H_3BTMB$ was synthesized by the method described in Tetrahedron 66 (2010) 3553-3563. Specifically, a mixture containing 1,3,5-tribromobenzene (0.500 g), m-methoxycarbonyl phenylboronic acid (1.0560 g), $K_3PO_4$ (2.3586 g), and $Pd(PPh_3)_4$ (0.0550 g) was stirred in 1,4-dioxane (50 mL) in a nitrogen atmosphere at 90° C. for 3 days. The reaction mixture was cooled to room temperature, and the solvent was evaporated. The residue was dissolved in $CH_2Cl_2$, washed with water, and dried over $MgSO_4$. The product was purified by silica gel column chromatography, which used $CH_2Cl_2$/n-hexane=(2:1→1:0) for elution, and the third main product was obtained. The obtained product was recrystallized with $CH_2Cl_2$/n-hexane. The recrystallized product was dissolved in 45 mL of MeOH, 25 mL of 6-N NaOH aqueous solution was added to the reaction mixture, and the mixture was refluxed at 95° C. overnight. The reaction mixture was cooled to room temperature, 20 mL of concentrated HCl was added thereto, and the mixture was stirred for 1 hour. The white precipitate was filtered and vacuum-dried, thereby obtaining $H_3BTMB$ with a yield of 88%. FIG. 1a) shows the single crystal X-ray structure of the resulting $H_3BTMB$. In the following Examples, anions derived from $H_3BTMB$ are noted as BTMB or $BTMB^{3-}$.

Example 1

Figure 2:
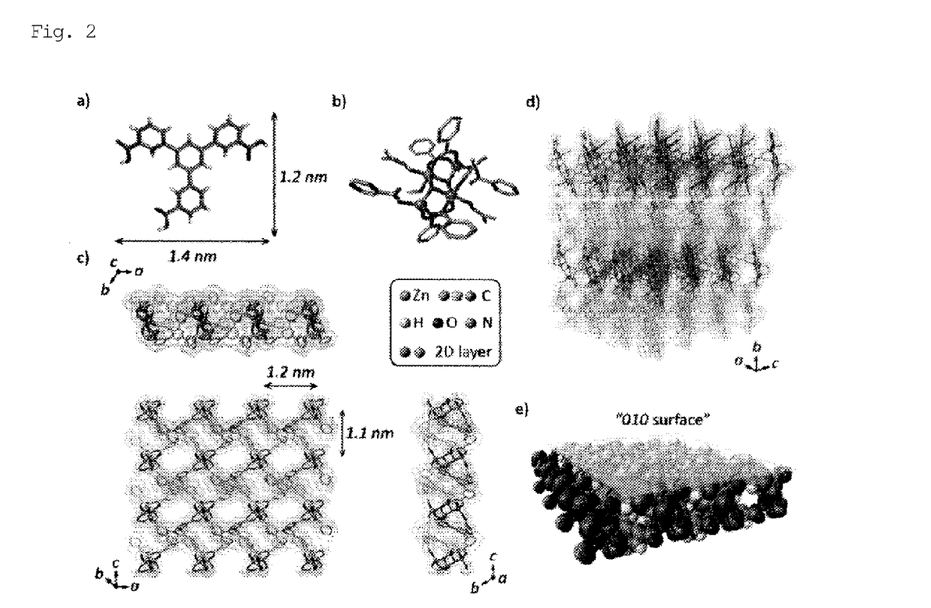
FIG. 2 schematically shows part of the structure of the porous coordination polymer (1) obtained in Example 1. a) shows the single crystal X-ray structure of $H_3BTMB$, b) shows the coordination environment around a $[Zn_4(\mu_3\text{-}OH)_2]$ cluster, c) shows a 2D layer structure, d) shows the 3D stacking structure of 2D layers, and e) shows the structure of the 010 surface.

A solid mixture of $H_3BTMB$ (11 mg, 0.025 mmol) and $Zn(NO_3)_2 \cdot 4H_2O$ (13 mg, 0.05 mmol) was dissolved in a mixed solution of $DMF/MeOH/H_2O$ (0.5 mL/0.25 mL/0.25 mL) in a 2-mL glass medicine bottle. To the reaction mixture, 20 µL of NaOH (0.01 M) was added as a deprotonation agent. The initial pH was 6.0. The entire reaction mixture was heated in a temperature-controllable oven from room temperature to 100° C. over 4 hours, and then heated at 100° C. for 48 hours. The oven was cooled from 100° C. to 30° C. over 6 hours. The resulting product, which contained uniform colorless flake-shaped crystals, was washed with MeOH, isolated, and air-dried. The actual amount was 15 mg, and the yield per mole of $H_3BTMB$ was 74%. The following single crystal X-ray diffraction etc., showed that single crystals of PCP (1) as synthesized had a structure of $[Zn_4(\mu_3\text{-}OH)_2(BTMB)_2(DMF)_3(MeOH)] \cdot (DMF)_2(H_2O)_2(MeOH)$ (FIGS. 1 and 2). FIG. 1 shows an ORTEP diagram, in which hydrogen atoms were omitted for clarity.

It was clarified that the single crystals of PCP (1) had a two-dimensional layered structure possessing two types of 1D channels along the b axis (FIG. 2c). Each layer comprises rhombus-shaped $[Zn_4(\mu_3\text{-}OH)_2]^{6+}$ tetranuclear clusters that are mutually connected though the $BTMB^{3-}$ ligands to form an (8,6) net. As shown in FIG. 2b), the $[Zn_4(\mu_3\text{-}OH)_2]^{6+}$ clusters each comprise two octahedral and two tetrahedral $Zn^{2+}$ ions, and two $\mu_3$-hydroxyl moieties ($OH^-$) that are located within three-atom mean planes formed by the metal centers. The octahedral $Zn^{2+}$ centers are bound to oxygen donors of three different carboxylate groups, both $OH^-$ fragments, and a solvent molecule, whereas the tetrahedral $Zn^{2+}$ centers are coordinated by oxygen atoms of three carboxylate groups and just one of the OH groups. Moreover, face-index measurement of the single crystals of PCP (1) identified the most dominant surface at the crystal surface as the (010) surface (FIG. 2e). The (010) surface possesses nano-scaled corrugation (with a periodicity of 1.2 nm×1.1 nm in the ac plane) arising from the aromatic portions of the $BTMB^{3-}$ ligand (FIGS. 2c) and 2e)).

Elemental microanalysis for $[Zn_4(\mu_3\text{-}OH)_2(BTMB)_2(DMF)_3(MeOH)] \cdot (DMF)_2(H_2O)_2(MeOH) \equiv C_{71}H_{79}N_5O_{23}Zn_4$ calculated (%): C, 52.25; H, 4.88; N, 4.29. Found (%): C, 52.04; H, 4.95; N, 4.03.

FT-IR (4000-525 $cm^{-1}$): 3615 (s, w), 3381 (br, w), 3061 (s, w), 2931 (s, w), 1648 (vs), 1611 (vs), 1590 (s), 1567 (vs), 1491 (w), 1441 (m), 1414 (m), 1371 (vs), 1267 (m), 1252 (m), 1160 (w), 1107 (m), 1077 (m), 1056 (w), 1032 (m), 874 (m), 802 (s), 763 (vs), 715 (m), 695 (s), 680 (vs), 652 (m), 618 (m).

Figure 3:
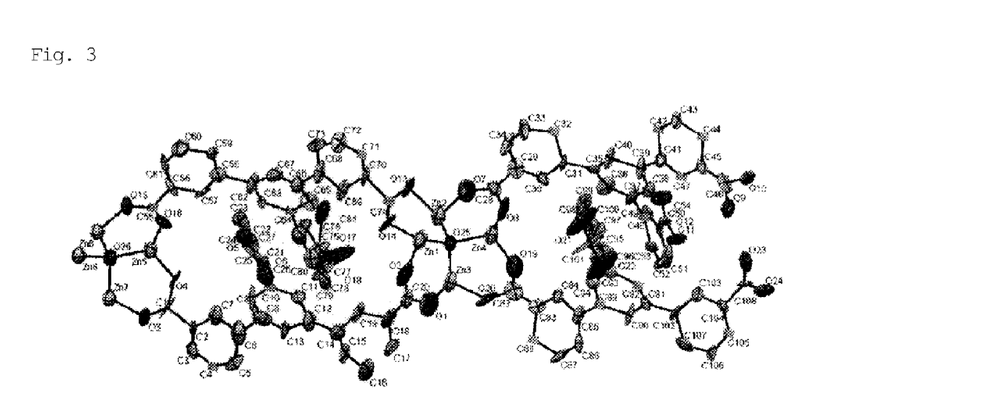
FIG. 3 shows an ORTEP diagram of a porous coordination polymer (1a) after degassing.
Figure 4:
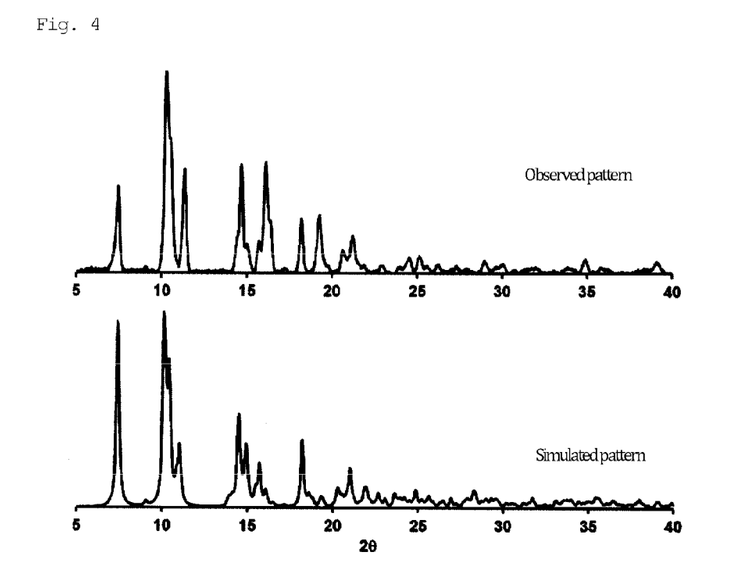
FIG. 4 shows the observed powder X-ray diffraction pattern of the degassed porous coordination polymer (1a) (upper graph), and the simulated powder X-ray diffraction pattern obtained from a single crystal.

PCP (1) as synthesized was heated at 250° C. for 2 hours and degassed to thereby obtain PCP (1a) having a structure of $[Zn_4(\mu_4\text{-}O)_2(BTMB)_2]$. FIG. 3 shows single crystal X-ray diffraction results of the degassed PCP (1a). FIG. 3 shows an ORTEP diagram, in which hydrogen atoms were omitted for clarity. Further, FIG. 4 shows the observed powder X-ray diffraction pattern of the degassed porous coordination polymer (1a) (upper graph), and the simulated powder X-ray diffraction pattern obtained from the single crystal. FIG. 4 demonstrates that the powder X-ray diffraction pattern of the degassed porous coordination polymer (1a) was reasonably matched with the simulated pattern obtained from the crystal structure file of the single crystal, and that PCP (1a) powder having a structure of $[Zn_4(\mu_4\text{-}O)_2(BTMB)_2]$ was synthesized and isolated.

Structural parameter for PCP (1a): Crystal system=triclinic, Space group=PI, a=13.394 (6), b=17.481 (6), c=26.185 (9), α=68.54 (5), β=73.59 (4), γ=74.59 (5), RI=22%, Rw=58%

Figure 5:
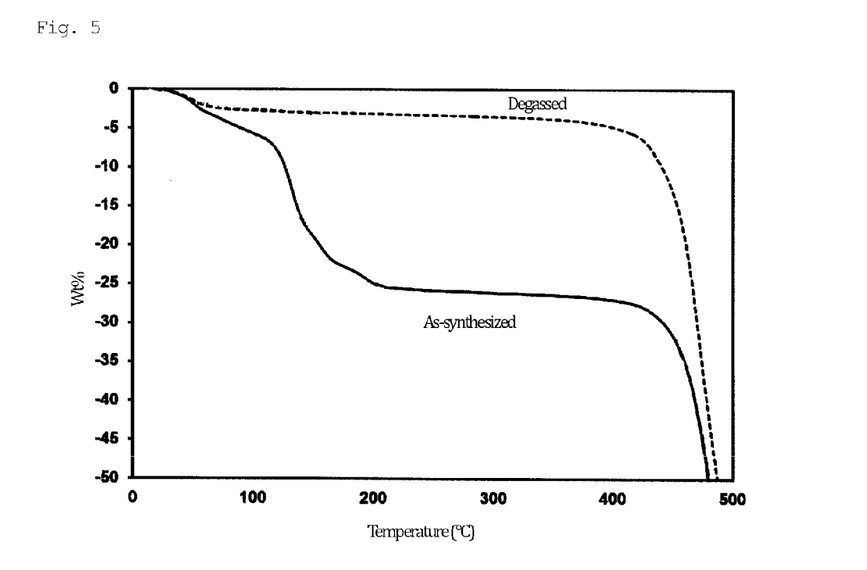
FIG. 5 shows the results of thermogravimetric analysis (TGA) of the degassed porous coordination polymer (1a) and the porous coordination polymer (1) as synthesized.

FIG. 5 shows the results of thermogravimetric analysis (TGA) of the degassed PCP (1a) and PCP (1) as synthesized. A weight loss of approximately 29% from the weight of PCP (1) as synthesized was observed. This value is close to 30%, which corresponds to the five DMF, two MeOH, and three $H_2O$ molecules (including one water molecule eliminated from the $Zn_4(OH)_2$ cluster) being removed from the formula unit of PCP (1) as synthesized. Moreover, FIG. 5 shows that the onset of the decomposition of the degassed PCP (1a) and PCP (1) as synthesized was around 410° C. This indicates that the porous coordination polymer of the present invention has good thermal stability, compared to conventional porous coordination polymers (decomposition onset temperature: around 350° C.) comprising a zinc ion and an organic ligand having $CO_2^-$.

Example 2 (Measurement of Contact Angles)

Figure 6:
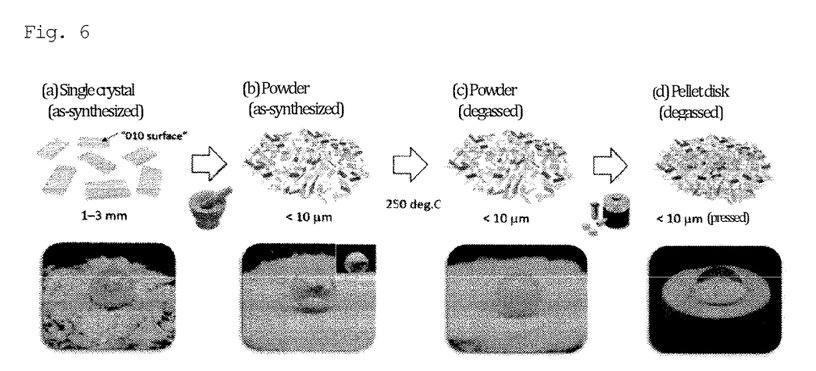
FIG. 6 schematically shows states of single crystals (a) of the porous coordination polymer (1) synthesized in Example 1, powder (b) obtained by finely grinding the single crystals of the porous coordination polymer (1), degassed powder (c), and a pellet (d) obtained by pressing the degassed powder at 5 MPa; and also shows photographs of a water droplet on each solid surface.

The contact angles of the single crystals (a) of PCP (1) synthesized in Example 1, powder (b) obtained by finely grinding the single crystals of PCP (1), degassed powder (c), and a pellet (d) obtained by pressing the degassed powder at 5 MPa were measured. FIG. 6 schematically shows four states of PCP (1) synthesized in Example 1, and photographs of a water droplet on each solid surface. The contact angle of the single crystals (a) was more than 150° (152°), and the roll-off angle was less than 10°, which is characteristic of a superhydrophobic solid. The results indicate that PCP (1) synthesized in Example 1 achieved superhydrophobicity due to the possession of the surface (010). Moreover, the powder (b) obtained by grinding the single crystals and the degassed powder (c) both had a contact angle of more than 150°, which indicated that they had superhydrophobicity. This reveals that the superhydrophobicity of PCP (1) synthesized in Example 1 was not affected by the presence of the solvent within the pores. On the other hand, the contact angle of the pressed pellet (d) was about 110°. This is considered to be because the surface was smoother, and roughness was reduced, due to compression at 5 MPa. These results reveal that the hierarchical structure in the powder is mainly responsible for the superhydrophobicity, and that surface roughness is reduced by applying pressure, thereby reducing the hydrophobicity.

Example 3 (Measurement of Adsorption Isotherms)

Figure 7:
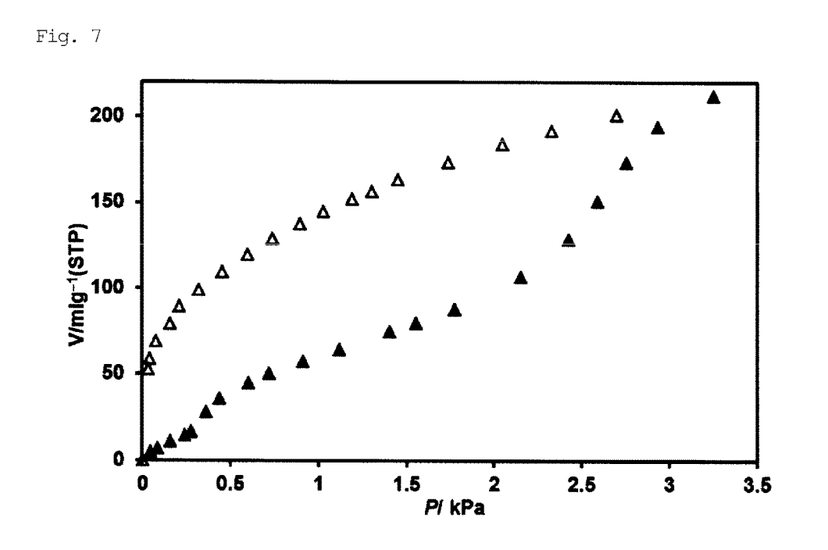
FIG. 7 shows the water adsorption isotherm of the degassed porous coordination polymer (1a) at 298 K.

In order to clarify the water adsorption capacity of the degassed PCP (1a), an adsorption isotherm experiment was conducted at 298 K. FIG. 7 shows the results. PCP (1a) showed unusual adsorption behavior, with two steps at 0.27 kPa and 2.3 kPa in the adsorption isotherm, and no steps in the desorption isotherm. This phenomenon is completely different from other superhydrophobic PCPs. The results of the water adsorption isotherm of PCP (1a) indicate that interior pore surfaces were not hydrophobic but were hydrophilic, and that only the exterior crystal surface exhibited superhydrophobicity. This phenomenon suggested that the superhydrophobicity of PCP (1a) originated from surface structural roughness rather than from chemical features of the surface. As was different from bulk water, water in the form of gas was easily adsorbed into the pores of PCP (1a).

Figure 8:
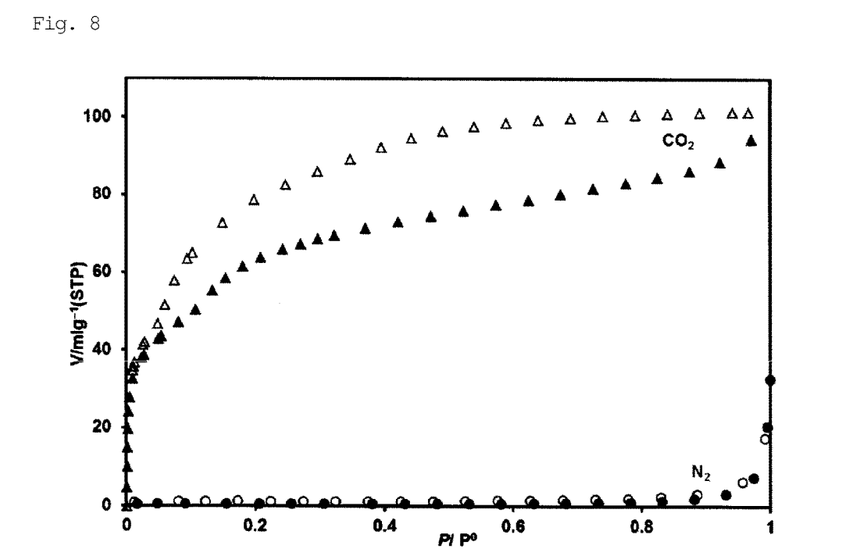
FIG. 8 shows the adsorption isotherms of the degassed porous coordination polymer (1a) for $CO_2$ at 195 K and $N_2$ at 77 K.

FIG. 8 shows the adsorption isotherms for $CO_2$ and $N_2$. The adsorption isotherm for $CO_2$ was measured at 195 K, and the adsorption isotherm for $N_2$ was measured at 77 K. The results of FIG. 8 indicated that $CO_2$ was adsorbed by PCP (1a) while $N_2$ was not adsorbed. Moreover, this $CO_2$ adsorption isotherm is a type-I isotherm, which is characteristic of micropores with permanent porosity.

Figure 9:
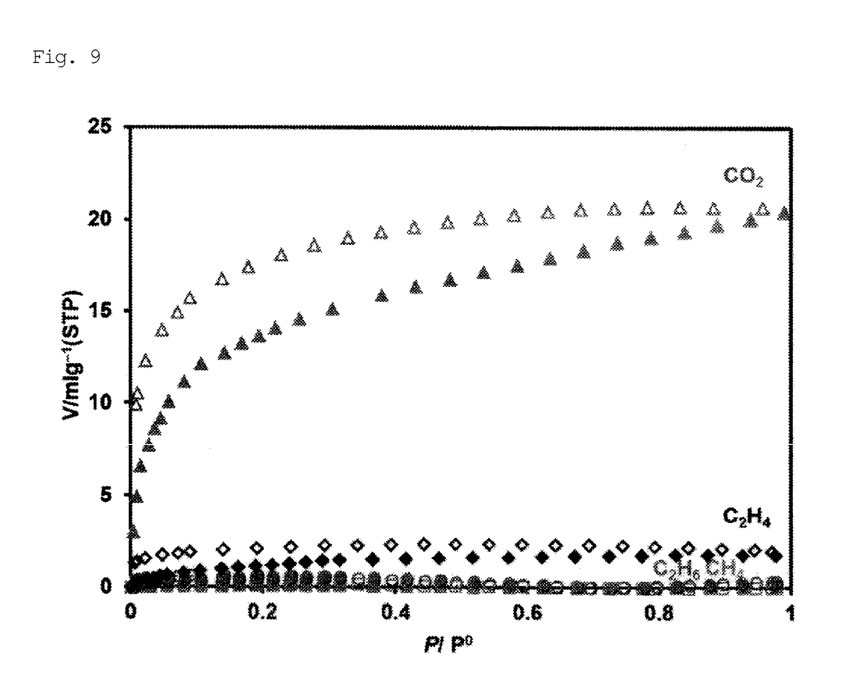
FIG. 9 shows the adsorption isotherms of the porous coordination polymer (containing acetone) activated at 100° C. for methane ($CH_4$), ethane ($C_2H_6$), ethylene ($C_2H_4$), and $CO_2$ at 195 K.

FIG. 9 shows the adsorption isotherms for methane ($CH_4$), ethane ($C_2H_6$), ethylene ($C_2H_4$), and $CO_2$ at 195 K. The PCP used in this case was obtained by changing the solvent contained in the pores of the PCP obtained in Example 1 to acetone, and performing degassing at 100° C. Consequently, it was found that $CH_4$, $C_2H_6$, and $C_2H_4$ were not adsorbed by PCP (1a).

Figure 10:
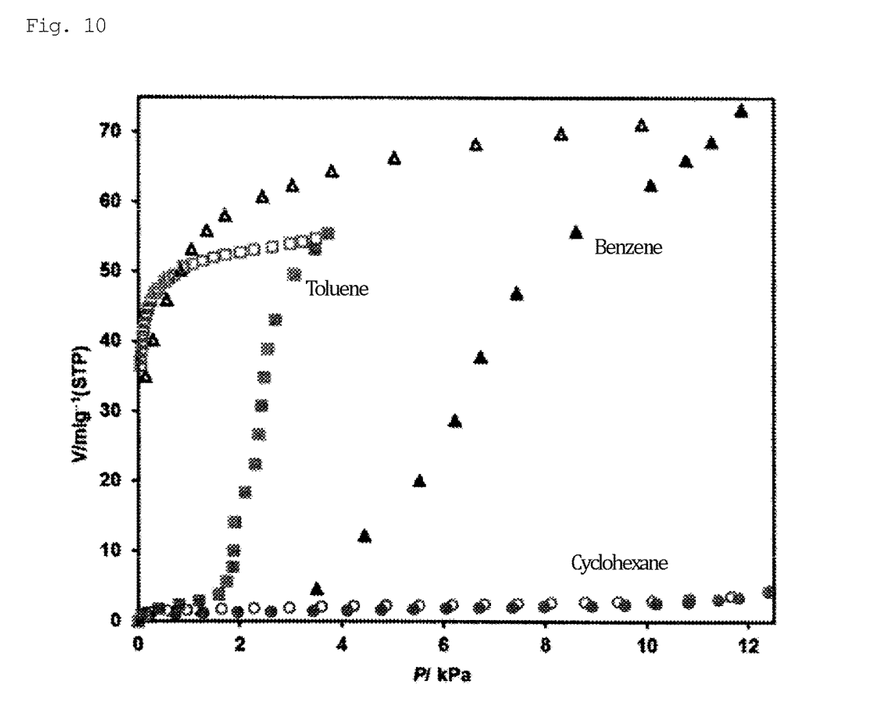
FIG. 10 shows the adsorption isotherms of the degassed porous coordination polymer (1a) for benzene, toluene, and cyclohexane at 298 K.

Further, in order to observe the adsorption capacity of PCP (1a) for 6-membered ring organic solvents, adsorption isotherms were measured for benzene, toluene, and cyclohexane at 298 K. FIG. 10 shows the results. The adsorption isotherms for benzene and toluene showed a gate-opening profile, whereas the adsorption isotherm for cyclohexane showed no adsorption. These results revealed that PCP (1a) had selectivity for size or aromaticity/aliphaticity.

Example 4 (Adsorption Experiment of Organic Solvents, Etc.)

Using the degassed PCP (1a), which had superhydrophobicity and porosity, an experiment was performed to remove organic solvents or oil from the water surface. In order to facilitate the operation, a pellet disk (area: approximately 2.2 cm$^2$) was produced by applying a pressure of 4 to 6 MPa to the degassed PCP (1a) powder. The organic solvents or oil used were toluene, benzene, cyclohexane, and olive oil, and they were colored blue with Oil Blue 35 so as to differentiate them from colorless water. The colored toluene was added dropwise on the water surface, and the pellet disk was dropped in the center of the toluene on the water surface. As a result, the pellet disk adsorbed the toluene. Then, the pellet disk adsorbing the toluene was taken out, thereby separating the toluene from water. The same results as toluene were obtained when benzene or olive oil was used in place of toluene. This revealed that the pellet disk of PCP (1a) could remove water-immiscible organic solvents, such as toluene and benzene, and olive oil from water.

Similarly, an experiment was performed to separate organic solvents or oil from the water surface using the degassed PCP (1a) powder. Water was placed in a glass medicine bottle, and while vigorously stirring, toluene colored blue with Oil Blue 35 was added. The PCP (1a) powder was dropped on the water surface while simultaneously stirring. The powder particles remained on the surface of water. When the powder adsorbing the toluene was filtered, the color of the PCP (1a) powder adsorbing the colored toluene was changed to blue. The same results as toluene were obtained when benzene or olive oil was used.

Figure 11:
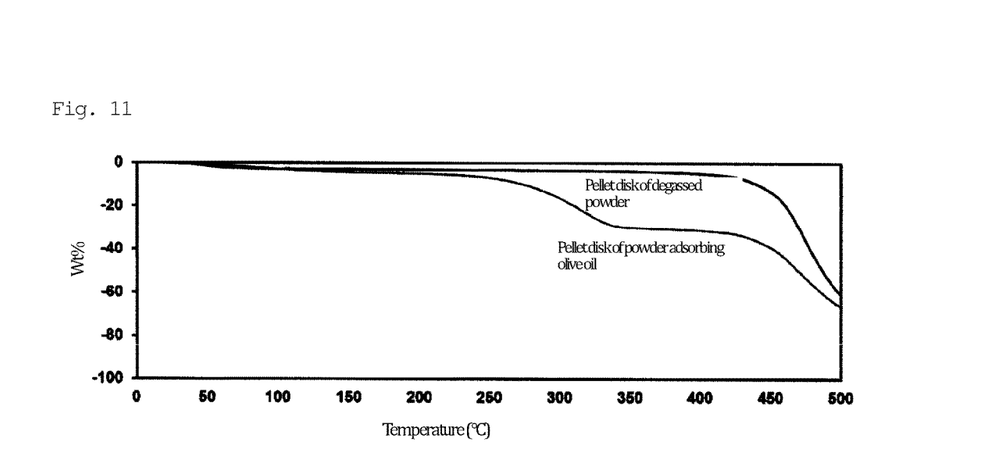
FIG. 11 shows the TGA results of a pellet disk of degassed porous coordination polymer powder, and a pellet disk adsorbing olive oil.

The adsorption of the organic solvents or oil from the water surface was quantitatively analyzed by TGA. FIG. 11 shows the results of a pellet disk of the PCP (1a) powder and a pellet disk adsorbing olive oil. According to the TGA of the powder adsorbing olive oil in FIG. 11, characteristic weight loss corresponding to the adsorbed oil was observed between 230 to 330° C. More qualitatively, 200 mg of PCP (1a) pellet disk having a surface area of approximately 2.2 cm$^2$ can adsorb approximately 420 wt % of olive oil. FIG. 11 also indicated that the skeleton of the powder that adsorbed the solvent or oil was as thermally stable as the degassed powder.

Figure 12:
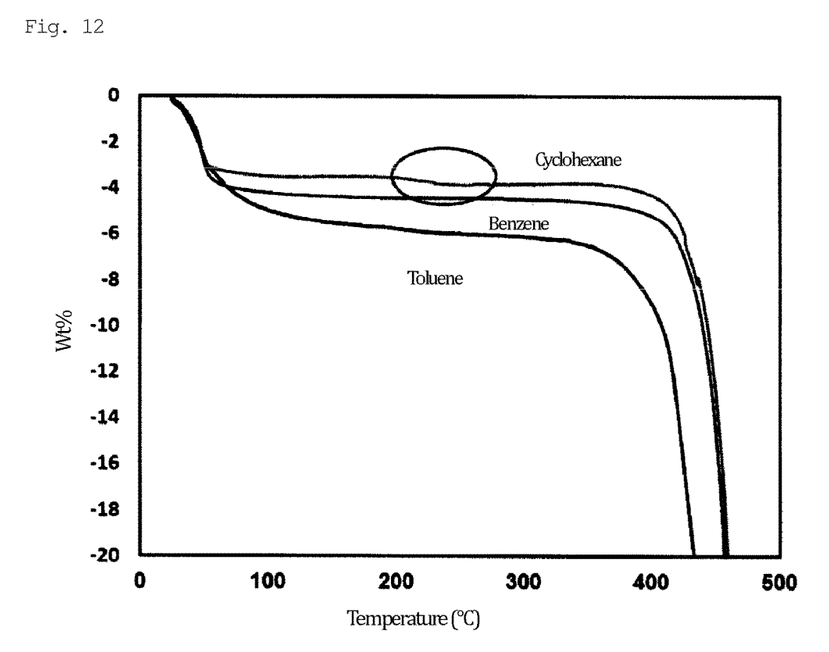
FIG. 12 shows the TGA results of toluene, benzene, and cyclohexane removed from the water surface.
Figure 13:
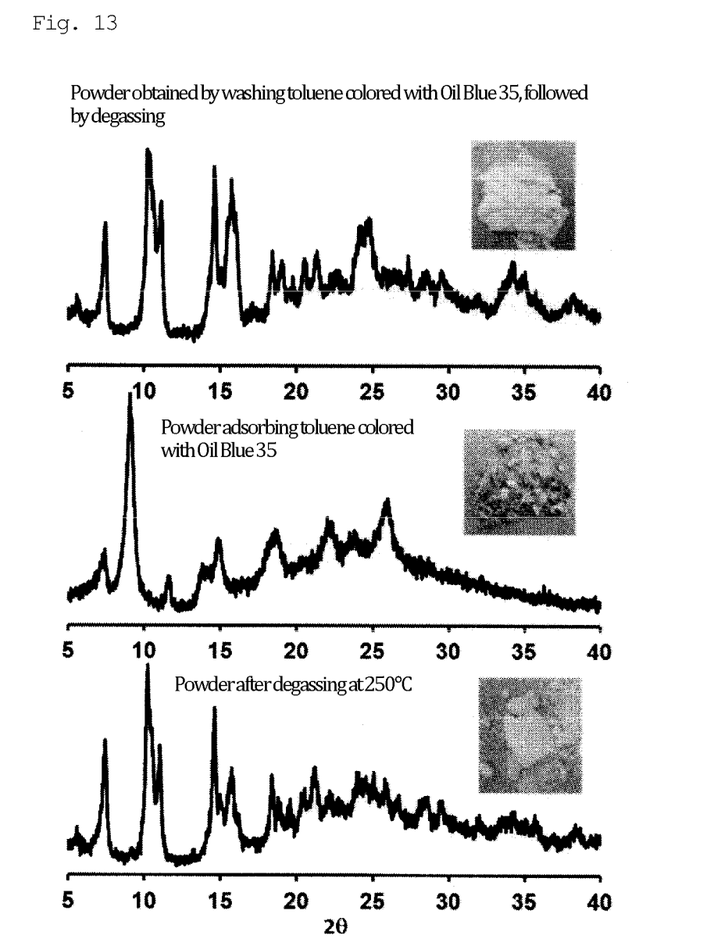
FIG. 13 shows X-ray diffraction patterns of degassed porous coordination polymer (1a) powder (lower graph), powder adsorbing toluene colored with Oil Blue 35 (middle graph), and powder obtained by washing with n-hexane toluene colored with Oil Blue 35, followed by degassing (upper graph).

TGA of the toluene, benzene, and cyclohexane removed from the water surface was measured. FIG. 12 shows the results. The circled portion of FIG. 12 corresponds to the weight loss of Oil Blue 35. FIG. 12 indicates that the toluene and benzene were adsorbed into the pores of PCP (1a) according to the general capillary phenomenon on the surface, while the cyclohexane was not adsorbed into the pores. The results were matched with the results of the adsorption isotherms for toluene, benzene, and cyclohexane in FIG. 10. Selective adsorption of aromatic solvents, such as toluene and benzene, rather than cyclohexane (aliphatic solvent) is attributable to the interaction with the aromatic BTMB ligand. Furthermore, FIG. 13 shows the X-ray diffraction patterns of the degassed PCP (1a) powder, a powder that adsorbed the toluene colored with Oil Blue 35, and a powder obtained by washing with n-hexane the toluene colored with Oil Blue 35, followed by degassing. The powder that adsorbed the toluene colored with Oil Blue 35 (middle graph) and the powder obtained by washing with n-hexane the toluene colored with Oil Blue 35 (upper graph) both had the same crystal structure as that of the degassed PCP (1a) powder (lower graph). These results demonstrate that the structure of PCP (1a) was stable even after the oil clean-up experiment was performed, and that it was reusable.

The invention claimed is:

1. A porous coordination polymer comprising:
   a divalent or trivalent metal ion; and
   an organic ligand represented by the following formula (1):

wherein $X^1$, $X^2$, and $X^3$ are the same or different, and each represent $CO_2^-$, $CS_2^-$, $PO_3^{2-}$, $PO_4^{2-}$, $AsO_3^{2-}$, $AsO_4^{2-}$, $SO_3^-$, $SO_4^-$, $SeO_3^-$, $SeO_4^-$, $TeO_3^-$, or $TeO_4^-$; and
$R^1$, $R^2$, $R^3$, $R^4$, $R^5$, $R^6$, $R^7$, $R^8$, $R^9$, $R^{10}$, $R^{11}$, and $R^{12}$ are the same or different, and each represent hydrogen or $C_{1-20}$ alkyl;
the metal ion and the organic ligand being alternately linked by a coordinate bond, and
the porous coordination polymer having a water contact angle of 150° or more.

2. The porous coordination polymer according to claim 1, wherein the organic ligand is a compound represented by the formula (1) wherein $X^1$, $X^2$, and $X^3$ are all $CO_2^-$; and $R^1$, $R^2$, $R^3$, $R^4$, $R^5$, $R^6$, $R^7$, $R^8$, $R^9$, $R^{10}$, $R^{11}$, and $R^{12}$ are all hydrogen.

3. The porous coordination polymer according to claim 1, wherein the metal ion is a transition metal ion.

4. The porous coordination polymer according to claim 1, wherein the metal ion is at least one member selected from the group consisting of zinc ions, nickel ions, and cobalt ions.

5. A hydrophobic coating agent comprising the porous coordination polymer according to claim 1.

6. An adsorbent for an organic solvent or oil, comprising the porous coordination polymer according to claim 1.

7. A hydrophobic coating agent comprising the porous coordination polymer according to claim 2.

8. A hydrophobic coating agent comprising the porous coordination polymer according to claim 3.

9. A hydrophobic coating agent comprising the porous coordination polymer according to claim 4.

10. An adsorbent for an organic solvent or oil, comprising the porous coordination polymer according to claim 2.

11. An adsorbent for an organic solvent or oil, comprising the porous coordination polymer according to claim 3.

12. An adsorbent for an organic solvent or oil, comprising the porous coordination polymer according to claim 4.

* * * * *